US00PP22428P3

(12) United States Plant Patent

Zaiger et al.

(10) Patent No.: US PP22,428 P3

(45) Date of Patent: Jan. 3, 2012

(54) INTERSPECIFIC TREE NAMED 'FALL FIESTA'

(50) Latin Name: ***Interspecific Prunus* species**
Varietal Denomination: Fall Fiesta

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 204 days.

(21) Appl. No.: 12/657,442

(22) Filed: Jan. 21, 2010

(65) Prior Publication Data

US 2011/0179533 P1 Jul. 21, 2011

(51) Int. Cl.
*A01H 5/00* (2006.01)

(52) U.S. Cl. ..... Plt./180

(58) Field of Classification Search ..... Plt./180
See application file for complete search history.

(56) References Cited

U.S. PATENT DOCUMENTS

PP12,409 P2 * 2/2002 Zaiger et al. ..... Plt./180

* cited by examiner

*Primary Examiner* — Wendy C Haas

(57) ABSTRACT

A new and distinct variety of interspecific *Prunus* tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Heavy and regular bearer of fruit.
3. Fruit with an attractive, blue black skin color.
4. Fruit with very good flavor and eating quality.
5. Fruit with good handling and shipping quality.
6. Fruit with an average Brix of 20° and a good balance between acid and sugar.

1 Drawing Sheet

Botanical classification: Interspecific *Prunus* species.
Variety denomination: 'Fall Fiesta'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plums, cherries and interspecific trees, which are known to us, and mentioned herein, are the proprietary interspecific seedling '178LM86', 'Dapple Fire' Interspecific (U.S. Plant Pat. No. 12,409), the proprietary plum seedling '321LC319' (unpatented) and the proprietary cherry seedling '5GK125' (unpatented).

STATEMENT REGARDING FEDERALLY SPONSORED RESEARCH AND DEVELOPMENT

Not applicable.

ORIGIN OF THE VARIETY

The new and distinct interspecific tree was originated by us from crosses between the following species [(*Prunus salicina*×*Prunus avium*)×(*Prunus salicina*×*Prunus persica*)]. The present variety was selected from a first generation cross between the proprietary selected seedling '178LM86' (unpatented) and 'Dapple Fire' Interspecific (U.S. Plant Pat. No. 12,409). The seed parent '178LM86' was developed and selected by us from a proprietary plum seedling selection '321LC319' crossed with a proprietary cherry seedling selection '5GK125'. We budded a large number of these seedlings to older 'Nemaguard' Rootstock (non-patented) trees to induce earlier fruit production for evaluation. Under close and careful observation the present seedling exhibited desirable fruit and tree characteristics, was selected in 2004 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree which includes [(Plum×Cherry)×(Plum×Plum Nectarine)×(Peach×Plum Peach)] in its parentage is of large size, vigorous, upright growth and a productive and regular bearer of medium to large size, yellow flesh, firm fruit with very good flavor and eating quality. The fruit is further characterized by holding firm on the tree 2 weeks after maturity (shipping ripe) and having good storage and shipping quality. In comparison to the seed parent '178LM86', the fruit of the new interspecific variety is larger in size, has firmer flesh, is approximately 30 days later in maturity, and has more desirable eating quality with less acidity. In comparison to the pollen parent 'Dapple Fire' Interspecific (U.S. Plant Pat. No. 12,409), the fruit of the new interspecific variety has yellow flesh, compared to red flesh, is slightly more elongated in shape, has blue black skin compared to red skin color and is approximately 10 weeks later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color in accordance with Munsell Book of Color.

Tree:

*Size.*—Large, pruned to 3 to 3.5 meters in height and width for economically harvesting of fruit. Varies with different cultural practices.

*Vigor.*—Vigorous, tree growth of approximately 1.5 to 2 meters the first growing season. Varies with cultural practices, soil type, fertility and climatic conditions.

*Form.*—Upright growth.

*Branching habit.*—Upright, crotch angle approximately 30°, increases with heavy crop.

*Productivity.*—Productive, thinning and spacing of fruit desirable for market size fruit.

*Bearer.*—Regular, adequate fruit set 3 consecutive years. No alternate bearing observed.

*Fertility.*—Self sterile, pollinator required.

*Density.*—Medium dense, usually pruned to vase shape to increase sunlight and air movement to center of tree to enhance fruit color and health of fruit spurs.

*Hardiness.*—Hardy in all stone fruit growing areas of California. Tree growing in USDA Hardiness Zone 9. Winter chilling requirement is approximately 800 hours at or below 45° F.

Trunk:

*Size.*—Medium to large. Average circumference of 43.5 cm at 32.0 cm above ground level on a 5 year old tree.

*Stocky.*—Medium.

*Texture.*—Medium shaggy, becomes rougher with age.

*Color.*—Varies from 10YR 7/2 to 7.5YR 6/2.

Branches:

*Size.*—Medium. Average circumference 17.9 cm at 1.0 meter above ground. Crotch angle approximately 30°, increases with heavy fruit crop.

*Surface texture.*—New growth smooth. Mature growth medium rough, roughness increases with age.

*Lenticels.*—Size — medium. Average number 44 in a 25.8 sq cm area. Average length 3.5 mm. Average width 1.2 mm. Color varies from 7.5YR 6/12 to 7.5YR 5/10.

*Color.*—New growth varies from 2.5GY 6/6 to 2.5GY 5/6. Old growth varies from 7.5YR 3/2 to 7.5YR 2/4, varies with age of growth.

Leaves:

*Size.*—Medium. Average length 92.3 mm. Average width 37.0 mm.

*Form.*—Oblanceolate.

*Apex.*—Acuminate.

*Base.*—Cuneate.

*Margin.*—Doubly serrate.

*Thickness.*—Medium.

*Surface texture.*—Upper surface relatively smooth, slight indentations over midrib and leaf veins. Lower surface relatively smooth, except for small ridges created by midrib and pinnate venation. Both upper and lower surfaces glabrous.

*Petiole.*—Average length 13.4 mm. Average width 1.5 mm. Longitudinally grooved. Surface — glabrous. Color varies from 2.5GY 7/4 to 5GY 7/6.

*Glands.*—Type — reniform. Size — medium. Average length 1.1 mm. Average diameter 0.4 mm. Average number 3, varies from 1 to 4. Located primarily on lower portion of leaf blade and upper portion of petiole. Color varies from 2.5GY 5/6 to 5GY 7/6.

*Color.*—Upper surface varies from 5GY 3/4 to 7.5GY 3/4. Lower surface varies from 5GY 4/4 to 7.5GY 4/4. Midvein color varies from 2.5GY 8/4 to 5GY 8/4.

Flower buds:

*Size.*—Small. Average length 8.1 mm. Average diameter 4.2 mm.

*Hardiness.*—Hardy with respect to California winters.

*Form.*—Conical, becoming elongated as it matures.

*Pedicel.*—Size — large. Average length 12.5 mm. Average width 0.6 mm. Color varies from 2.5GY 7/8 to 2.5GY 6/10. Surface — glabrous.

*Color.*—N 9.5/(white).

*Number of buds per spur.*—Average 7, varies from 5 to 10. Varies with age of spur.

Flowers:

*Blooming period.*—Date of First bloom Mar. 2, 2009. Date of Petal Fall Mar. 11, 2009, varies slightly with climatic conditions.

*Size.*—Small to medium. Average height 11.4 mm. Average diameter 18.5 mm.

*Petals.*—Number — normally 5, alternately arranged to sepals. Size — small. Average length 8.6 mm. Average width 6.3 mm. Form — varies from globose to slightly elongated. Margin — sinuate. Both upper and lower surfaces glabrous. Color N 9.5/(white).

*Sepals.*—Number — normally 5, alternately arranged to petals. Size — small. Average length 2.6 mm. Average width 2.5 mm. Shape — triangular, apex rounded. Both upper and lower surfaces glabrous. Color — upper surface 5GY 5/6 to 5GY 5/8. Lower surface varies from 5GY 5/6 to 5GY 5/8.

*Stamens.*—Average number per flower 29, varies from 28 to 30. Average filament length 8.4 mm. Filament color N 9.5/(white). Anther color varies from 7.5YR 6/10 to 5Y 8/10.

*Pollen.*—Self sterile, pollinator required. Color varies from 2.5Y 7/10 to 2.5Y 6/10.

*Pistil.*—Normally one. Surface glabrous. Average length 9.3 mm. Position of stigma approximately 0.7 mm below anthers. Color varies from 10Y 8/6 to 10Y 7/8.

*Fragrance.*—Slight aroma.

*Color.*—N 9.5/(white).

*Number flowers per flower bud.*—Average number 2, varies from 1 to 3.

*Pedicel.*—Average length 15.8 mm. Average width 0.7 mm. Color varies from 2.5Y 7/8 to 2.5GY 6/8. Surface glabrous.

Fruit:

*Maturity when described.*—Firm ripe.

*Date of first picking.*—Sep. 19, 2009.

*Date of last picking.*—Sep. 29, 2009, varies slightly with climatic conditions.

*Size.*—Medium to large. Average diameter axially 68.9 mm. Average transversely in suture plane 63.9 mm. Average weight 167.6 grams, average weight varies slightly with fertility of the soil, amount of thinning and climatic conditions.

*Form.*—Slightly elongated.

*Suture.*—Nearly smooth, extends from base to apex.

*Ventral surface.*—Nearly smooth.

*Apex.*—Rounded.

*Base.*—Flat to very slightly retuse.

*Stem cavity.*—Rounded to slightly elongated in suture plane. Average depth 5.3 mm. Average diameter 4.1 mm.

Stem:

*Size.*—Medium to large. Average length 16.5 mm. Average diameter 2.7 mm.

*Color.*—Varies from 5GY 6/6 to 10YR 4/4.

Flesh:

*Ripens.*—Evenly.

*Texture.*—Firm, meaty.

*Fibers.*—Few, small and tender.

*Firmness.*—Good, comparable to commercial varieties.

*Aroma.*—Slight.

*Amydgalin.*—Undetected.

*Eating quality.*—Very good.

*Flavor.*—Very good, good balance between acid and sugar.

*Juice.*—Heavy to moderate, enhances flavor.

*Brix.*—Average Brix 20°, varies slightly with amount of fruit per tree and climatic conditions.

*Color.*—Yellow, varies from 10YR 7/10 to 10YR 6/10.

*Pit cavity.*—Ovoid to globose. Average length 29.7 mm. Average width 21.2 mm. Color varies from 10YR 7/10 to 10YR 5/10.

Skin:

*Thickness.*—Medium.

*Surface.*—Relatively smooth, very slightly waffled.

*Pubescence.*—None present.

*Tendency to crack.*—Very slight with heavy rain, varies with fruit maturity.

*Color.*—Ground color yellow, varies from 2.5Y 8.5/6 to 2.5Y 8/8. Overspread with 5R 2/2 to 7.5R 2/6.

*Tenacity.*—Tenacious to flesh.

*Astringency.*—Undetected.

Stone:

*Type.*—Semi-clingstone.

*Size.*—Medium to large. Average length 28.6 mm. Average width 19.5 mm. Average thickness 10.3 mm.

*Form.*—Ovoid.

*Base.*—Flat.

*Apex.*—Pointed. Average length 1.3 mm.

*Surface.*—Very small pits throughout.

*Sides.*—Unequal, one side extending further outward from suture plane.

*Ridges.*—A small narrow ridge on each side of suture extending from base toward apex.

*Tendency to split.*—None.

*Color.*—Varies from 7.5YR 5/6 to 10YR 6/4.

Kernel:

*Size.*—Average length 16.8 mm. Average width 11.5 mm. Average depth 5.7 mm.

*Form.*—Ovoid.

*Viability.*—Viable, embryo fully developed.

*Skin.*—Color varies from 10YR 6/6 to 10YR 5/8.

Use: Dessert.

*Market.*—Local and long distance.

Keeping quality: Good, held firm in cold storage for 3 weeks at 38° to 42° F. without shriveled, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

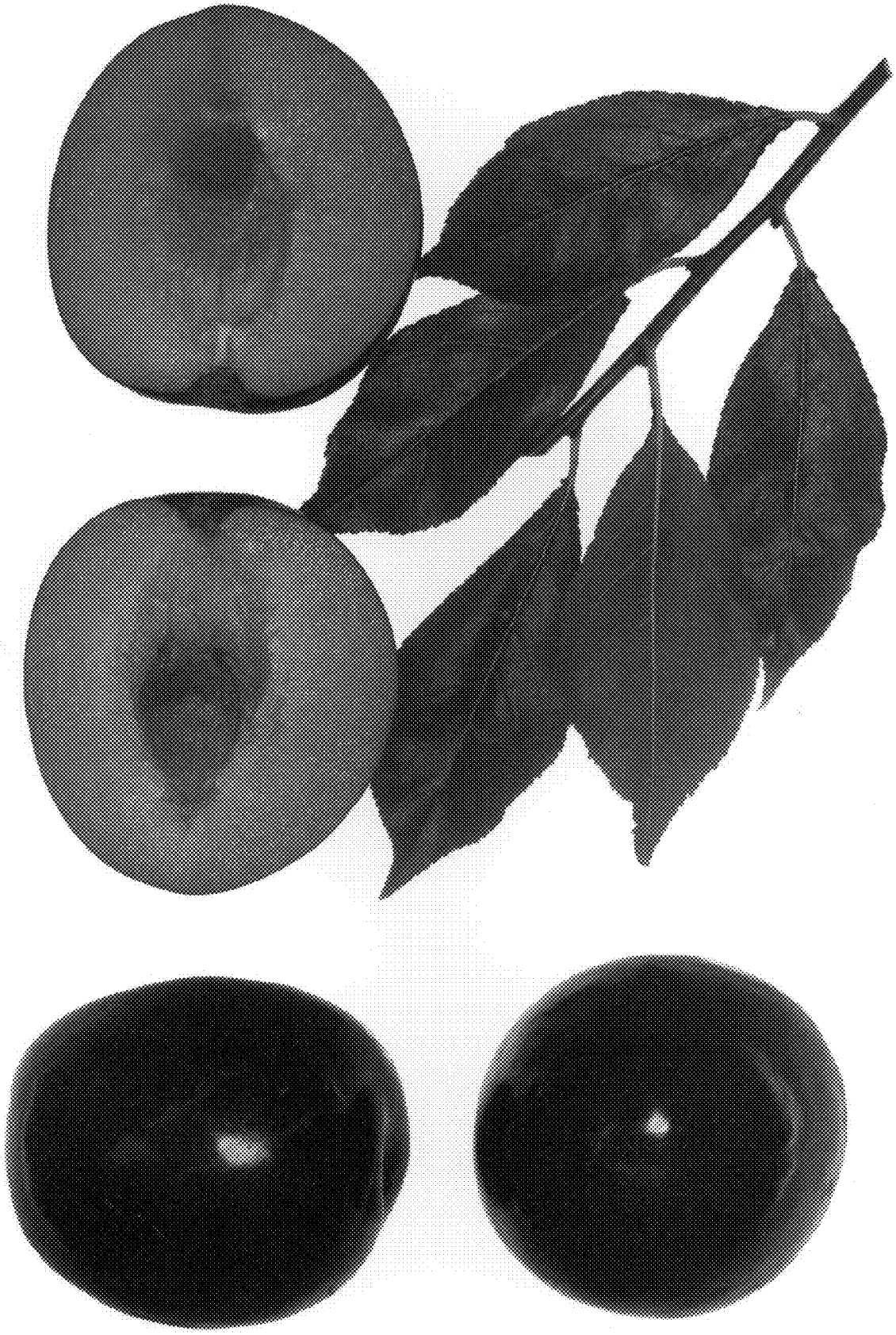

* * * * *